(12) United States Patent
Freeman et al.

(10) Patent No.: US 8,068,905 B2
(45) Date of Patent: Nov. 29, 2011

(54) METHOD AND APPARATUS FOR CONTINUOUS ELECTRODE IMPEDANCE MONITORING

(75) Inventors: Warwick Freeman, Box Hill (AU); Philip Grasso, Box Hill (AU); Richard Newman, Templestowe (AU)

(73) Assignee: Compumedics Limited, Abbotsford, Victoria (AU)

( * ) Notice: Subject to any disclaimer, the term of this patent is extended or adjusted under 35 U.S.C. 154(b) by 55 days.

(21) Appl. No.: 11/205,373

(22) Filed: Aug. 17, 2005

(65) Prior Publication Data

US 2006/0020218 A1    Jan. 26, 2006

(51) Int. Cl.
*A61B 5/05*    (2006.01)
*A61B 5/04*    (2006.01)
*G01R 27/02*    (2006.01)

(52) U.S. Cl. ........ 600/547; 600/509; 600/544; 600/546; 324/602

(58) Field of Classification Search .......... 600/544–548, 600/509–525; 324/600–727
See application file for complete search history.

(56) References Cited

U.S. PATENT DOCUMENTS

| | | | | |
|---|---|---|---|---|
| 4,459,993 A * | 7/1984 | Foreman | | 600/519 |
| 4,610,254 A * | 9/1986 | Morgan et al. | | 607/6 |
| 4,870,341 A * | 9/1989 | Pihl et al. | | 324/600 |
| 4,919,145 A * | 4/1990 | Marriott | | 600/536 |
| 4,993,423 A | 2/1991 | Stice | | |
| 5,042,498 A | 8/1991 | Dukes | | |
| 5,184,616 A * | 2/1993 | Weiss | | 607/4 |
| 5,300,093 A * | 4/1994 | Koestner et al. | | 607/32 |
| 5,819,741 A * | 10/1998 | Karlsson et al. | | 600/523 |
| 6,007,532 A | 12/1999 | Netherly | | |
| 6,487,449 B1 * | 11/2002 | Kaiser et al. | | 600/547 |
| 7,020,513 B2 * | 3/2006 | Faisandier | | 600/547 |
| 2002/0046756 A1 * | 4/2002 | Laizzo et al. | | 128/899 |

* cited by examiner

Primary Examiner — Max Hindenburg
Assistant Examiner — John Pani
(74) Attorney, Agent, or Firm — Briggs and Morgan, P.A.

(57) ABSTRACT

In one embodiment, the present invention includes a test signal generator capable of producing an impedance test signal comprising of a sine wave having a known frequency. The test signal generator may include a crystal oscillator, a counter, and a lookup table. The lookup table output is applied to a digital to analog converter and is then low pass filtered using a conventional analog filter to produce a sine wave of a known frequency and voltage amplitude. The test signal flows through the electrode and combines with an electrophysiological signal to form a combined signal. A signal processor is used to isolate the combined signal into the test signal component and the electrophysiological component. The signal processor digitally low pass filters the combined signal and the output of the low pass filter is the electrophysiological signal. The signal processor then digitally bandpass filters the combined signal using a filter with a center frequency which is the same as the test frequency. The output of this filter is then used to calculate the electrode impedance.

8 Claims, 4 Drawing Sheets

METHOD AND APPARATUS FOR CONTINUOUS ELECTRODE IMPEDANCE MONITORING

FIELD OF THE INVENTION

Generally, the present invention relates to a method and apparatus for ensuring the accuracy of an acquired physiological signal. More specifically, the present invention is a method of monitoring electrode impedance while receiving an electromagnetic physiological signal.

BACKGROUND OF THE INVENTION

Physiological monitors will often have a testing procedure to check whether the interface between a sensor and the patient being monitored is adequate to acquire a physiological reading. This is especially true with regards to the acquisition of an electrophysiological signal. Typically, an electrophysiological signal is acquired through an electrode which is attached to the patient. The contact between an electrode and a patient's skin can significantly affect the results of an electrophysiological signal. High contact impedance generally causes poor quality recordings due to power interference.

It is a common practice to measure the electrode to skin contact impedance before the start of an electrophysiological recording session. This is done by injecting a small alternating current, Ie, into the electrode and measuring the voltage, Ve, produced across the electrode. The electrode impedance, Ze, may be calculated from the equation $Ze=Ve/Ie$.

However, most physiological monitors cannot monitor physiological signals during an impedance test because the contact impedance test interferes with the acquisition of the electrophysiological signal. Electrophysiological signals such as EEG, ECG, EOG and EMG are often distorted by the test current utilized during the test. Consequently, the prior art devices have been unable to continuously monitor the contact impedance between the electrode and the patient.

It is not uncommon for electrodes to partially or fully detach from a patient during monitoring, and such an occurrence can seriously distort the electrophysiological signal acquired from the patient. Furthermore, it is often too difficult to visually monitor each electrode on a patient. Consequently, there is a need for an apparatus and a method to continuously monitor the contact impedance between an electrode and a patient without preventing the acquisition of an electrophysiological signal.

SUMMARY OF THE INVENTION

The present invention is a method and apparatus for continuously monitoring a test signal while simultaneously acquiring a physiological signal. The impedance test methods currently employed in electrophysiological recording equipment cause interference to the signal being recorded because the test signal has a frequency (or frequencies in the case of non-sinusoidal test waveforms) within the frequency band of the electrophysiological signal. By shifting the test signal to a slightly higher frequency than the electrophysiological signal a digital signal processor (DSP) can be used to low pass filter a received signal to recover and discern the electrophysiological signal from the test signal. A digital band pass filter of the DSP can be used to extract the impedance test signal and electrode impedance from the received signal.

In one embodiment, the present invention includes a test signal generator capable of producing an impedance test signal comprising of a sine wave having a known frequency. The test signal generator includes a crystal oscillator, a counter, and a lookup table. The lookup table output is applied to a digital to analog converter and is then low pass filtered using a conventional analog filter to produce a test signal comprised of a sine wave having a known frequency and voltage amplitude. The test signal is passed through the electrode and combines with an electrophysiological signal to form a combined signal.

In one embodiment, a signal processor is used to isolate the combined signal into the test signal component and the electrophysiological component. The signal processor digitally low pass filters the combined signal and the output of the low pass filter is the electrophysiological signal. The signal processor then digitally bandpass filters the combined signal using a filter with a center frequency which is the same as the test frequency. The output of this filter is then used to calculate the electrode impedance.

In one embodiment, the present invention can be adapted to be integrated into an electrophysological monitoring system such as EEG, EOG, EMG, and ECG. The contact impedance between an electrode and a patient can be continuously monitored while simultaneously acquiring an electrophysiological signal. A display can be used to monitor both the physiological signal and the contact impedance.

BRIEF DESCRIPTION OF THE DRAWINGS

In this disclosure, only certain embodiments are depicted, and not all or every insubstantial change or modification of each such embodiment are depicted or described herein, although those of ordinary skill in the art to which the invention is directed will appreciate many insubstantial changes to the teaching of this disclosure that nevertheless fall within the spirit and scope of the invention. In this disclosure, reference numerals are used to refer to various elements, sub-elements and process steps and the same reference numeral is intended to denote all similar or identical elements set forth herein.

DETAILED DESCRIPTION OF THE INVENTION

The present invention is a method and apparatus for change in electrode impedance monitoring via a combined test and physiological signal. While the embodiment disclosed is particularly adapted to monitor contact impedance and EEG, ECG, EOG, or EMG signals, one skilled in the art can readily adapt the present invention to monitor different parameters, which involve the testing of a sensor that is acquiring a physiological signal.

Figure 1:
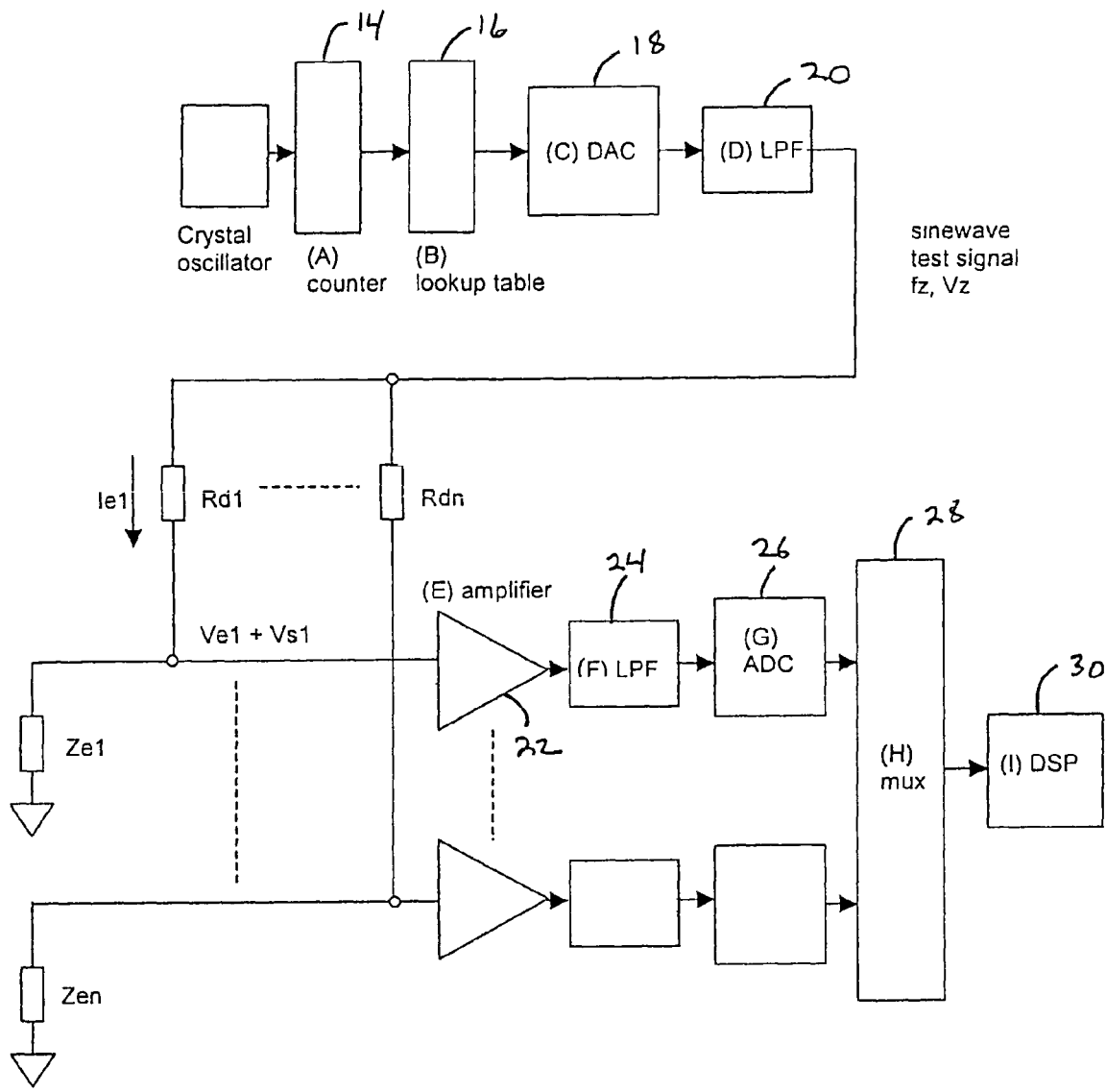
FIG. 1 is a block diagram of one embodiment of the present invention.

As shown in FIG. 1, in one embodiment, the present invention includes a test signal generator capable of producing an impedance test signal comprising of a sine wave having a known frequency, fz 3, which is slightly higher than the frequency range of the electrophysiological signal being monitored. A crystal oscillator 12 provides a known, frequency stable signal to clock the input of a counter 14. The counter output sequentially accesses a lookup table 16 which can be implemented using any digital storage device such as an EPROM or RAM, containing a sine waveform in digital format. The lookup table 16 output is then applied to a digital to analog converter (DAC) 18. The output of the DAC is low pass filtered using a conventional analog filter 20 to produce a sine wave of frequency, fz, and voltage amplitude Vz.

A resistor, Rd1, with a resistance many times higher than the desired electrode impedance range, converts Vz into a test current Ie1. This current flows through the electrode, represented in FIG. 1 by Ze1, to produce a voltage, Ve1, at the input of amplifier 22. There will also be an electrophysiological signal, Vs1, at the input of amplifier 22. The combined signal of Ve1+Vs1 is amplified and then low pass filtered by anti-aliasing filter 24 before being converted into a digital signal by analog to digital converter (ADC) 26. The resultant digital signal is read by a digital signal processor (DSP) 30 via multiplexor 28. FIG. 1 shows the concept of the present invention extended to n electrode channels, using a separate ADC 26 for each channel, but a single ADC with an analog multiplexor would work equally well.

The ADC sampling frequency should be greater than twice fz to prevent aliasing. The DSP 30 should have sufficient computational power to execute both filters for all channels at the desired sample rate plus any storage or display functions. It should be noted that the DSP 30 could alter the sampling frequency, fs, signal bandwidth, fo, and impedance test frequency, fz, provided the relationship to each other is maintained as per FIG. 2.

Figure 2:
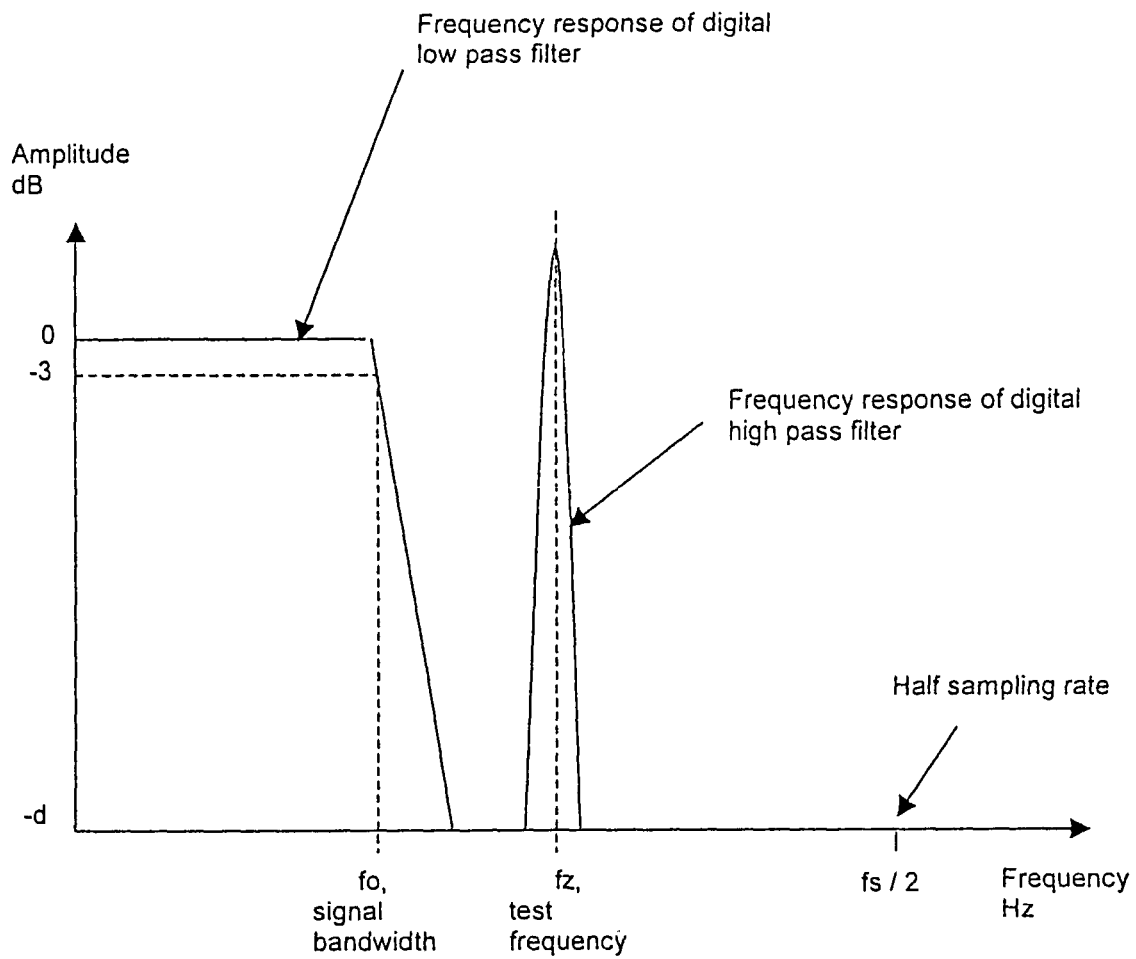
FIG. 2 is a graph of the relationship between a test frequency and a frequency of an electrophysiological signal.

In one embodiment, the combined signal can be isolated into the test signal component and the electrophysiological component by filtering the combined signal at appropriate frequencies. The DSP 30 digitally low pass filters the combined signal using a filter with a −3 dB point, fo, which is lower than the impedance test frequency, fz as shown in FIG. 2. The physiological signal, Vs1, alone is the output of the low pass filter. The low pass filter should have a sharp roll-off characteristic so that the test signal component at fz is completely removed. The filter should also have a linear phase characteristic so the physiological signal is not distorted. A symmetrical FIR filter (finite impulse response) can be readily designed to meet both these requirements.

The DSP 30 also digitally bandpass filters the combined signal using a filter with a center frequency of fz, the same as the test frequency. The output of this filter is Ve1, as the physiological signal and any higher frequency noise has been removed by the bandpass filter. The bandpass filter may be implemented as either an FIR or an IIR (infinite impulse response) if shorter computation time is needed.

The electrode impedance, Ze, can then be calculated as Ze=Ve1/Ie1, where Ie1=Vz/Rd1, which is a constant. In one example Vz would be 1 volt pk-pk and Rd1=20 megohms, giving Ie1=50 nanoampers pk-pk. Thus Ve1 will be 50 microvolts pk-pk per kilohm of electrode impedance. The impedance of each electrode could be displayed numerically on a computer monitor connected to the DSP (FIGS. 3 and 4) or used to activate indicators such as light emitting diodes attached to the amplifier circuit enclosure should the impedance exceed a pre-determined threshold.

Figure 3:
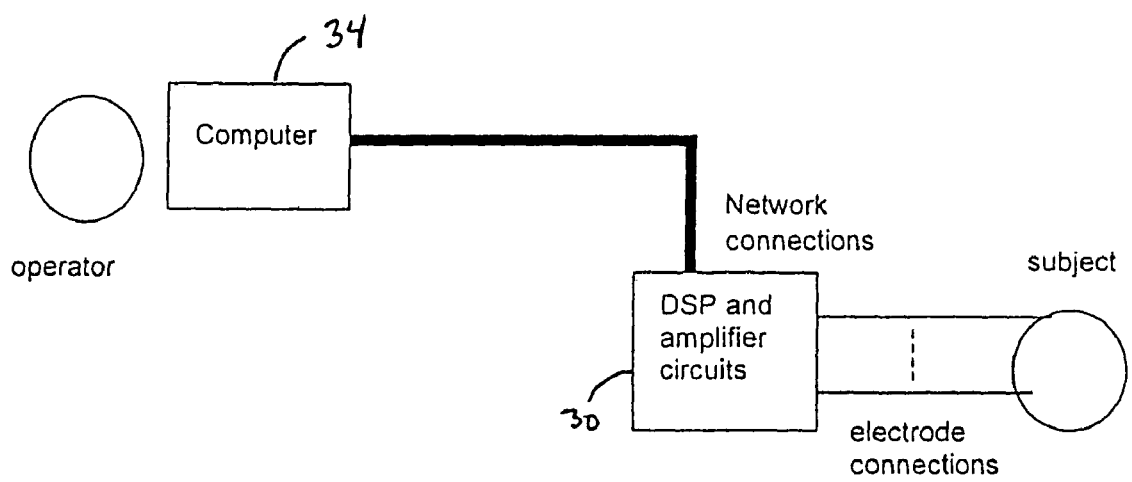
FIG. 3 is a block diagram of a system employing one embodiment of the present invention.
Figure 4:
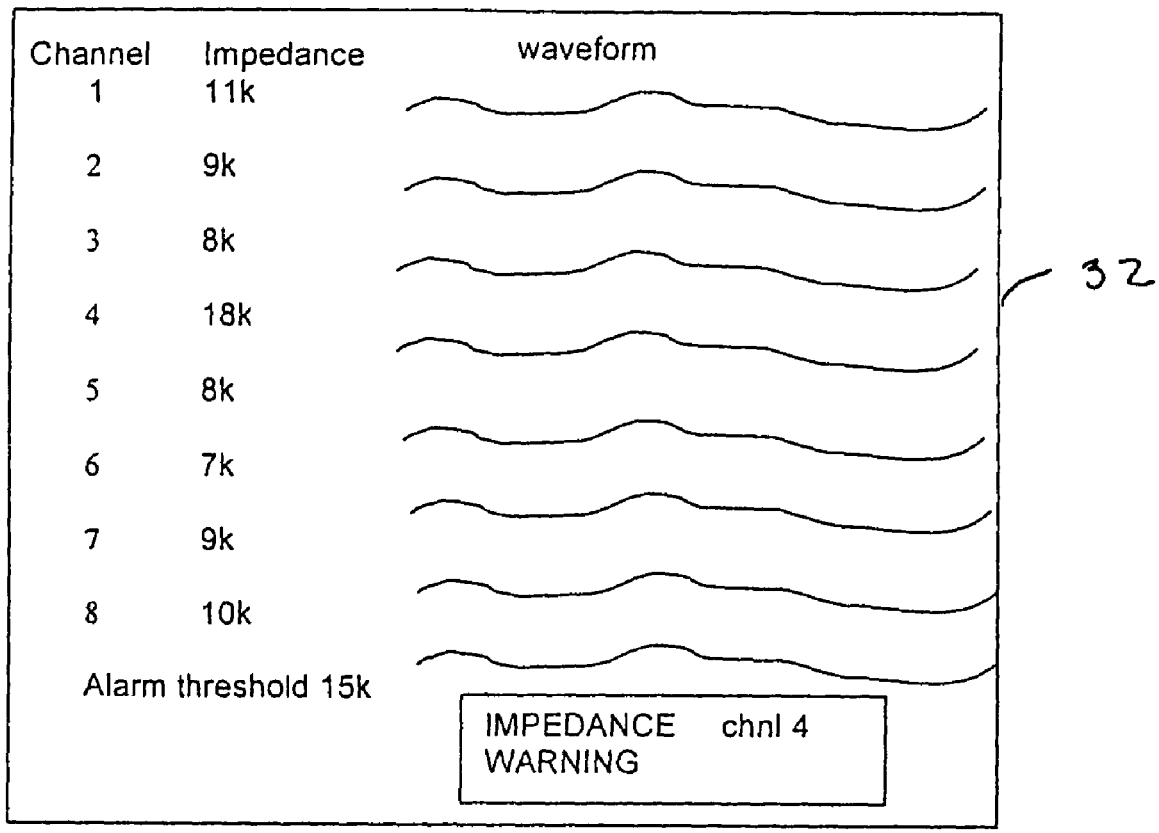
FIG. 4 is an embodiment of a display in one embodiment of the present invention.

As shown in FIGS. 3 and 4, in one embodiment, the present invention can be adapted to be integrated into an electrophysiological monitoring system 30 such as EEG, EOG, EMG, and ECG. The contact impedance between an electrode and a patient can be continuously monitored while simultaneously acquiring an electrophysiological signal. A display 32 can be used to monitor both the physiological signal and the contact impedance.

In one embodiment, the electrophysiological monitor system 30 may also communicate with a central monitoring station 34. The electrophysiological monitor system 30 is adapted to trigger an alarm condition at the central monitoring station 34 should the impedance of any of the electrodes exceed a pre-determined threshold for a pre-determined time (to avoid spurious values triggering the alarm). The operator could set the alarm threshold and the minimum time the threshold needs to be exceeded before the alarm is triggered via a computer network connection to the electrophysiological monitor system 30. This would allow an operator to monitor the contact impedance of each electrode for each patient at a central location remote from the electrophysiological monitor system 30.

The matter set forth in the foregoing description and accompanying drawings is offered by way of illustration only and not as a limitation. While a particular embodiment has been shown and described, it will be obvious to those skilled in the art that changes and modifications may be made without departing from the broader aspects of applicant's contribution. The actual scope of the protection sought is intended to be defined in the following claims when viewed in their proper perspective based on the prior art.

We claim:

1. A method comprising:
acquiring a physiological signal through an electrode sensor in contact with a location on a patient's body;
providing a frequency stable signal;
clocking an input of a counter with the frequency stable signal to produce a counter output,
accessing a lookup table with the counter output to produce a lookup table output;
applying the lookup table output to a digital to analog converter to produce a digital to analog converter output;
low pass filtering the digital to analog converter output to produce an impedance test signal comprising a sine wave having a voltage amplitude, $V_z$, and a known frequency which is higher than a frequency range of the physiological signal being monitored;
converting the voltage amplitude, $V_z$, into a test current, $I_{e1}$;
at the same time as said acquiring, sending the test current, $I_{e1}$, from the electrode sensor in contact with the location on the patient's body to produce a test signal having a voltage component, $V_{e1}$;
receiving a combined signal comprising the physiological signal and the test signal, wherein the physiological signal has a voltage component, $V_{s1}$;
low pass filtering the combined signal to isolate the voltage component, $V_{s1}$, of the physiological signal;
band pass filtering the combined signal to isolate the voltage component, $V_{e1}$, of the test signal and create a band pass filter output;
calculating a contact impedance between the electrode sensor and the patient by dividing the band pass filter output by the test current, $I_{e1}$; and
simultaneously displaying the physiological signal and the contact impedance.

2. The method of claim 1, wherein the physiological signal is selected from the group consisting of an electroencephalogram (EEG) signal, an electrocardiogram (ECG) signal, an electrooculogram (EOG) signal, and an electromyogram (EMG) signal.

3. The method of claim 1, wherein converting the voltage amplitude, $V_z$, into the test current, $I_{e1}$, includes using a resistor with a resistance that is higher than a desired electrode impedance range.

4. The method of claim 1, further comprising activating an indicator if the contact impedance exceeds a pre-determined threshold.

5. A method comprising:
acquiring a physiological signal through an electrode in contact with a location on a patient's body, said physiological signal being communicated via a line to a monitor system, wherein the physiological signal has a voltage component, $V_{s1}$;
providing a frequency stable signal;
clocking an input of a counter with the frequency stable signal to produce a counter output;
accessing a lookup table with the counter output to produce a lookup table output;
applying the lookup table output to a digital to analog converter to produce a digital to analog converter output;
low pass filtering the digital to analog converter output to produce an impedance test signal comprising a sine wave having a voltage amplitude, $V_z$, and a known frequency which is higher than a frequency range of the physiological signal;
converting the voltage amplitude, $V_z$, into a test current, $I_{e1}$;
during said acquiring, sending the test current, $I_{e1}$, from the electrode in contact with the location on the patient's body to produce a test signal having a voltage component, $V_{e1}$, said test signal being communicated via said line;
combining the physiological signal with the test signal to create a combined signal;
at said monitor system, deriving a physiological waveform from the combined signal by low pass filtering the combined signal to isolate the voltage component, $V_{s1}$, of the physiological signal;
band pass filtering the combined signal to isolate the voltage component, $V_{e1}$, of the test signal and create a band pass filter output;
calculating a contact impedance between the electrode and the patient by dividing the band pass filter output by the test current, $I_{e1}$; and
simultaneously displaying the physiological waveform and the contact impedance from the combined signal.

6. The method of claim 5, wherein the physiological signal is selected from the group consisting of an electroencephalogram (EEG) signal, an electrocardiogram (ECG) signal, an electrooculogram (EOG) signal, and an electromyogram (EMG) signal.

7. The method of claim 5, wherein converting the voltage amplitude, $V_z$, into the test current, $I_{e1}$, includes using a resistor with a resistance that is higher than a desired electrode impedance range.

8. The method of claim 5, further comprising activating an indicator if the contact impedance exceeds a pre-determined threshold.

* * * * *